United States Patent [19]

Drake, Jr.

[11] Patent Number: 4,720,628
[45] Date of Patent: Jan. 19, 1988

[54] OPTICAL PROCESS FOR DETERMINING THE ENDPOINT OF A PROCESS VIA ANALOG MULTIPLICATION OF PHOTOCELL SIGNALS

[75] Inventor: Herbert G. Drake, Jr., San Rafael, Calif.

[73] Assignee: Tegal Corporation, Novato, Calif.

[21] Appl. No.: 923,367

[22] Filed: Oct. 27, 1986

[51] Int. Cl.⁴ .............................................. G01J 1/42
[52] U.S. Cl. ................................. 250/214 R; 356/224
[58] Field of Search ............... 250/214 R, 214 A, 208, 250/209; 356/224, 228, 229

[56] References Cited

U.S. PATENT DOCUMENTS

| | | | |
|---|---|---|---|
| 3,664,752 | 5/1972 | Hermieu | 356/224 |
| 3,687,558 | 8/1972 | Rex | 356/224 |
| 4,320,289 | 3/1982 | White et al. | 250/214 R |
| 4,465,370 | 8/1984 | Yuasa et al. | 356/224 |

Primary Examiner—David C. Nelms
Assistant Examiner—William L. Oen
Attorney, Agent, or Firm—Paul F. Wille

[57] ABSTRACT

An improved optical endpoint detector is disclosed in which two photocells are used in conjunction with analog multipliers and variable voltage sources, all under microprocessor control. The combination enables one to measure the ratio of intensity of different emission lines, as well as their individual outputs and alternative process monitoring signals.

11 Claims, 4 Drawing Figures

OPTICAL PROCESS FOR DETERMINING THE ENDPOINT OF A PROCESS VIA ANALOG MULTIPLICATION OF PHOTOCELL SIGNALS

BACKGROUND OF THE INVENTION

This invention relates to optical monitoring of processes and, in particular, to monitoring the emissions from a plasma glow discharge for determining the optimum endpoint of a process.

It has been recognized for a long time that the optical emission from a plasma glow discharge, as with any luminous source, is characteristic of that discharge. This fact has been used to determine the endpoint of a process step by detecting a change in the emission; for example, its intensity or color. U.S. Pat. No. 4,312,732, for example, discloses a system for detecting endpoint on the basis of the intensity of the light emitted by the glow discharge. When the intensity, as represented by a variable voltage, reaches some predetermined level, the process is terminated. U.S. Pat. No. 4,246,060 discloses a system for detecting a temporary uniformity of the voltage as indicative of optimal endpoint.

While these techniques are suitable for certain processes, there are many for which they are not. Further, the equipment maker has a fundamental problem of providing general purpose equipment. The alternative, making equipment suitable for only one process, e.g. etching a particular layer overlying a specific material using a certain gas mixture, is very expensive, both for the manufacturer and the consumer.

Thus, one needs to make equipment as flexible as possible. In addition, the sensitivity of the endpoint detection apparatus must be improved so that useful nuances can be detected in the glow discharge. For example, in an etch process where the underlying film has a relatively small exposed area, it is difficult to detect when the plasma has penetrated film. Thus the optical emissions may be too small to detect with prior designs or difficult to distinguish from noise.

For other processes, one may want to add, subtract, multiply, divide and/or differentiate the signals from more than one photocell. Providing any one of these functions is not particularly difficult. Providing all of them in as simple and least costly manner as possible is not as easy.

Another problem is system errors. In a plasma reactor having multiple photocells, one cannot be sure that the differences in intensity from various inputs are due to changes in the glow discharge. The location and transparency of the port may cause spurious readings, particularly if polymers or other materials accumulate on one port more quickly than on another. Also, pressure, power, or gas mixture changes can cause common mode changes in photocell outputs.

In view of the foregoing, it is therefore an object of the present invention to provide an improved apparatus for detecting changes in a luminous process.

Another object of the present invention is to provide apparatus for performing mathematical operations on analog signals from photocells to help detection of endpoint on films with low exposed areas.

A further object of the present invention is to provide apparatus which can be easily configured to perform a variety of analyses on analog signals from photocells.

Another object of the present invention is to provide endpoint detection apparatus which is less susceptible to system errors.

Another object of the present invention is to provide a normalization servomechanisms that ensures that each process generating an endpoint signal that is initialized at a level specified in the application recipe.

SUMMARY OF THE INVENTION

The foregoing objects are achieved in the present invention wherein a pair of photocells are connected to analog multiplier circuits by multiplex circuits. At least one of the multiplex circuits also has reference and bias signals applied to the inputs thereof for application to a multiplier. Another of the multiplex circuits feeds the output of one multiplier to the input of the other. The outputs of the multipliers are further amplified and processed. The multiplex circuits, reference signals, and amplifiers are all under computer control to select either photocell individually or various ratio functions. An ability to select a third process dependent function (e.g. DC bias) is also provided.

BRIEF DESCRIPTION OF THE DRAWINGS

A more complete understanding of the present invention can be obtained by considering the following detailed description in conjunction with the accompanying drawings, in which.

DETAILED DESCRIPTION OF THE INVENTION

Figure 1:
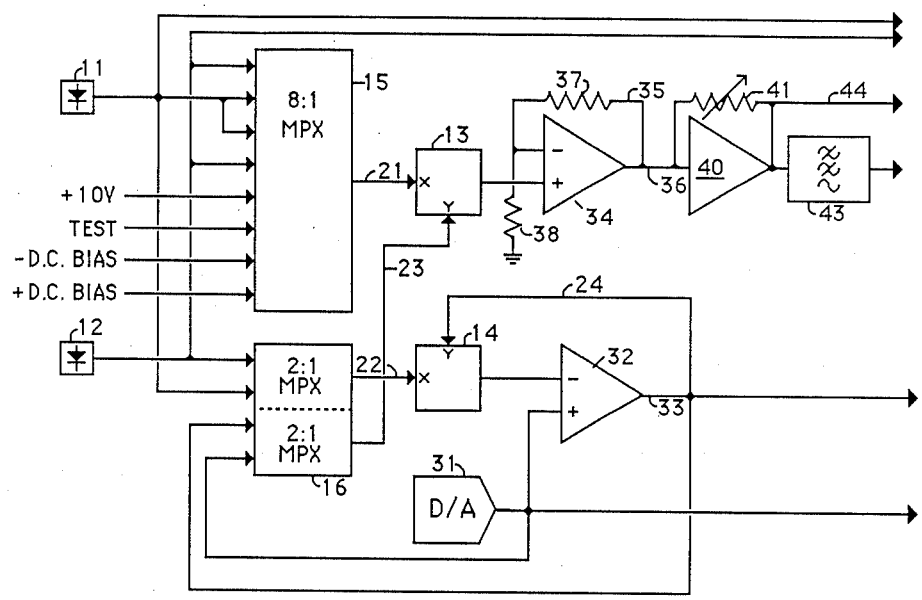
FIG. 1 illustrates a preferred embodiment of an endpoint detector circuit in accordance with the present invention.

As illustrated in FIG. 1, photocells 11 and 12 are connected in various combinations to multipliers 13 and 14 by way of multiplex circuits 15 and 16, respectively. Multiplex circuits 15 and 16 are the semiconductor equivalent of single pole multiple position switches. Specifically, multiplexer 15 corresponds to a single pole eight position switch with the pole connected to output 21. Multiplexer 16 corresponds to a pair of single pole double throw switches with the poles connected to outputs 22 and 23, respectively. Multiplex circuits 15 and 16 can comprise any suitable device and in a preferred embodiment comprise semiconductor devices functioning under the control of a data bus (not shown). Multiplexer 15 requires three bits to define the positions of the switch. Multiplexer 16 comprises two single pole double throw switches, each requiring one bit to define the position of the switch. Thus, a total of five bits of information is necessary to fully drive multiplexers 15 and 16.

Analog multipliers 13 and 14 can comprise any suitable device and in one embodiment of the present invention comprise an integrated circuit identified by the number AD532, as sold by Analog Devices. These multipliers, depending upon applied bias signals, produce an output proportional to the product of the inputs.

The output of multiplier 13 is connected to the non-inverting input of amplifier 34. The inverting input of amplifier 34 is connected to feedback loop 35 comprising resistors 37 and 38 connected in series. The inverting input of amplifier 34 is connected to the tap between resistors 37 and 38. Thus amplifier 34 multiplies the output from multiplier 13 by a specific amount. Output 36 from amplifier 34 is connected amplifying means 40 having a variable feedback loop 41 for adjusting the gain thereof. The output from amplifying means 40 is connected to low pass filter 43 to attenuate high frequency components in the signal or is available directly by way of output 44.

The output of multiplier 14 is connected to the inverting input of amplifier 32. The non-inverting input of amplifier 32 is connected D/A converter 31, which in one embodiment of the present invention comprise a twelve bit D/A converter circuit. Output 33 of amplifier 32 is connected to one input of multiplier 14, forming a feedback loop. As thus configured, amplifier 32 provides an output signal which is a predetermined multiple of the ratio of the output voltage from D/A converter 31 to the voltage on input line 22. During a predetermined normalization interval, a servomechanism (not part of FIG. 1) adjusts D/A converter 31 until the endpoint signal at 44 reaches a specified starting point. As the normalization period continues, this servomechanism tracks changes in the input signal(s), holding the output constant. When the normalization interval is over, the D/A is frozen and the output is dependent on the selected mathematical process.

Figure 2:
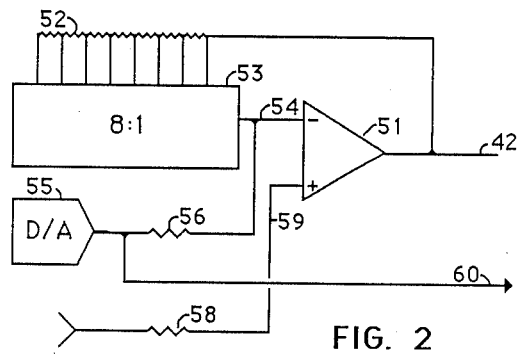
FIG. 2 illustrates in greater detail a portion of the circuit of FIG. 1.

FIG. 2 illustrates in greater detail amplifying means 40. Specifically, amplifying means 40 comprises operational amplifier 51 having a plurality of resistances 52 series connected in a feedback loop. Interconnecting the junctions of resistors 52 and the inverting input of amplifier 51 is multiplex circuit 53. As with multiplex circuit 15, multiplex circuit 53 corresponds to a single pole eight position switch. Also as with multiplex circuit 15, multiplex circuit 53 is fully driven by a three bit data bus (not shown). Thus, by providing the appropriate data to multiplex circuit 53, one controls the resistance in the feedback path and hence the gain of amplifier 51.

The inverting input of amplifier 51 acts as a summation point for the output from multiplexer 53 and eight bit D/A converter 55. D/A converter 55 is connected to line 54 by way of resistor 56. The non-inverting input of amplifier 51 is connected by way of resistor 58 to the output of amplifier 34, illustrated in FIG. 1 as connected to line 36.

In operation, multiplexer 53 is provided with a three bit code to determine the gain of amplifier 51. D/A converter 55 is provided with an eight bit code to produce a predetermined output voltage representing the normalization voltage (the set point used by the normalization servomechanism described above). This D/A converter output, in addition to providing a setpoint for the normalization servomechanism by way of line 60, is coupled by way of resistor 56 to input line 51. These data thus control the operating point and gain of amplifier 51 and ensure that the normalization servomechanism does not back out the selected gain value. The analog input signal on line 59 to the non-inverting input of amplifier 51 is thus amplified a predetermined amount and coupled to output line 42. By controlling the gain of amplifier 51, one controls the sensitivity of the apparatus and assures that the variations of interest are passed on to the output, for example, to a chart recorder or further signal processing equipment, well known per se in the art, such as for threshold or first and second derivative detection.

Figure 3:
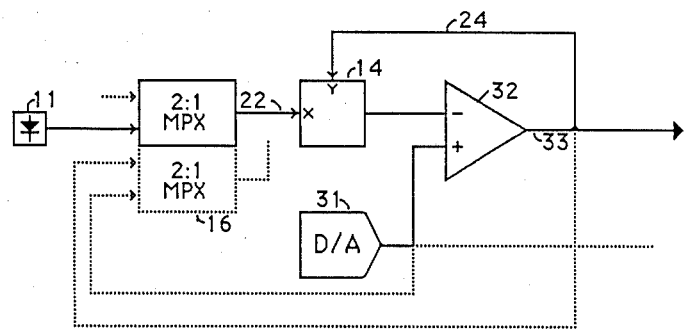
FIG. 3 illustrates one mode of operation of the present invention.

FIG. 3 illustrates the operation of the circuit of FIG. 1 in which the output of photocell 11 is monitored. Specifically, multiplexer 16 is programmed to connect photocell 11 to output 22 and to one input of multiplier 14. The other input to multiplier 14 is derived from the output of amplifier 32 which has its inverting input connected to the output of multiplier 14. The non-inverting input of amplifier 12 is connected to D/A converter 31. In this configuration, the output voltage on line 33 is equal to ten times the voltage from D/A converter 31 divided by the voltage from photocell 11. Since the output from multiplier 14 is connected to the inverting input of amplifier 32, the voltage from photocell 11 becomes a divisor. Thus, one can monitor the luminosity of the process, or a particular emission line thereof, and adjust the gain of the circuit by varying the voltage from D/A converter 31. This D/A converter is adjusted during the normalization interval to provide the gain needed to obtain the desired endpoint signal at the start of a process. The adjustment is controlled by the normalization servomechanism.

By virtue of the operation of the upper half of multiplexer 16, one can easily select either photocell for application to multiplier 14.

Figure 4:
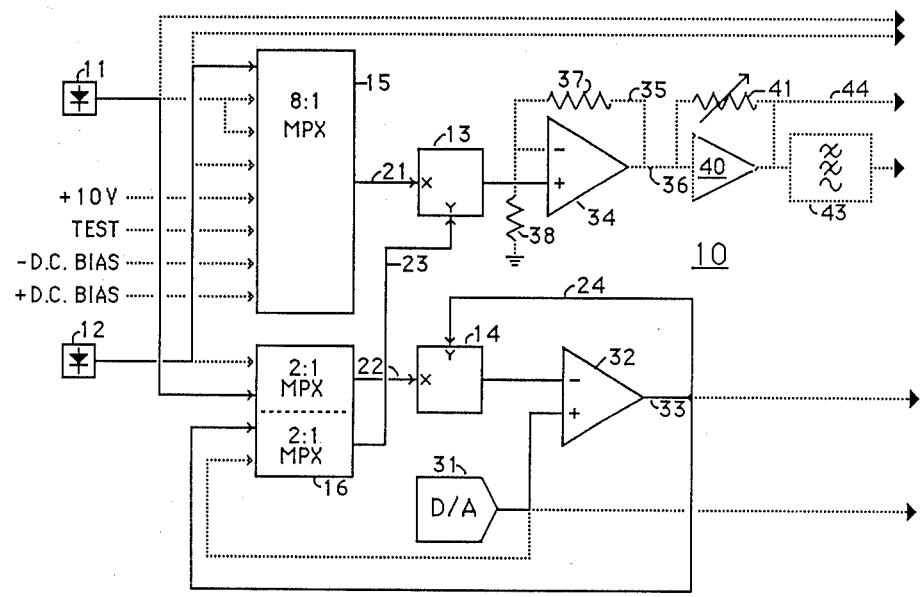
FIG. 4 illustrates the ratio mode of operation of the present invention.

FIG. 4 illustrates the operation of the present invention wherein one is obtaining the ratio of the outputs from photocells 11 and 12. In this configuration, photocell 11 is connected to multiplier 14 as is the case in FIG. 3. Photocell 12 is connected to multiplier 13 by way of multiplexer 15. The output from amplifier 32 is as described above. In this case, however, the output is coupled to the second input of multiplier 13 by way of the lower portion of multiplexer 16. The output from multiplier 13 is then applied to the non-inverting input of amplifier 34. In this configuration, the output from multiplier 13 is equal to the voltage from photocell 12 divided by the voltage from photocell 11 times the voltage from D/A converter 31. Thus, one can easily divide the two signals and control the magnitude of the result simply by adjusting the digital number provided to D/A converter 31. This provides for the same normalization process as does a single cell application since the D/A counter output voltage remains in the numerator of the transfer function.

By virtue of multiplexers 15 and 16, one can easily reverse the connections of the photocell and obtain the ratio of the output from photocell 11 to the output from photocell 12.

In plasma processing, one can sense the end of an etch, for example, by the change in luminosity of the glow discharge or a portion of the glow discharge. This change is converted to a voltage change by photocells 11 and 12. An endpoint is interpreted as the luminosity dropping below a threshold voltage. This threshold voltage, either positive or negative, is set with the apparatus of the present invention by applying the output signal from 43 or 44 to an analog to digital converter (not shown), which allows a microprocessor to track the process being monitored. Software is provided which, in addition to controllers the multiplexers and operating parameters of the circuitry shown, is capable of triggering endpoint by applying threshold, rate of change, or rate of rate of change (zero, first, or second time derivative) criteria to this signal.

As an alternative to endpoints based on photocell devices, the implementation shown is able to function with alternate signal sources that vary during the process. One of these is the level of self-generated DC bias that is produced by the plasma. When it is desired to apply DC bias criteria for determining endpoint, and the polarity of the DC bias signal is known, multiplexer 15 can be set to route the desired signal into multiplier 13. The other input to multiplier 13 is provided by D/A converter 31 by way of multiplexer 16. The output from multiplier 13 is the bias voltage divided by ten, times the voltage from D/A converter 31. This voltage is then coupled through amplifiers 34 and 40 to an output wherein it can be used to establish a reference. Other signals can be supplied to multiplexer 15 and passed to multiplier 13 to provide for self-testing this circuitry under software control by comparing the output voltage obtained to the expected output voltage from D/A converter 31.

There is thus provided by the present invention a flexible, easily configured system for processing analog signals from photocells and other signals that vary as a process takes place. Because the photocells are isolated from any summation node, the circuit is more immune to RF interference. Further, the output from the photocells can be manipulated without feedback to the photocell itself. Specifically, by virtue of D/A converter 31, the magnitude of the product can be controlled. Also, by virtue of the multiplexers and multipliers, one can readily obtain a variety of combinations of signals to detect endpoint. For example, magnitude, and the ratio of one signal to another or the other signal to the one.

Having thus described the invention it will be apparent to those of skill in the art that various modifications can be made within the spirit and scope of the present invention. For example, various voltage sensing circuits for detecting an out of range condition can easily be added to the circuit of the present invention. Similarly, the multiplex circuits can be driven by any suitable computer or I/O device. In one embodiment of the present invention multiplexer 15 comprised a CMOS 4051 circuit as sold by Motorola, Inc. and others. Multiplexer 15 comprised a CMOS 4053 multiplexer as sold by Motorola, Inc. and others. D/A converter 31 comprised a MC3408 digital-to-analog circuit as sold by Motorola, Inc. It is understood by those of skill in the art that the indication of particular integrated circuits for implementing the present invention is by way of example only and is not intended to be limiting. Photocells 11 and 12 need not be sensing different areas of the process chamber. It is preferred to use a single optical fiber pickup which is then split to couple light to each photocell. In this way system errors can be reduced.

I claim:

1. Apparatus for monitoring a luminous process comprising:

plural photocell means each producing an electrical signal dependent upon the luminosity of said process;

analog multiplier means for producing an electrical signal proportional to the product of electrical signals; and multiplex means for interconnecting said photocell means and said analog multiplier means in predetermined combinations.

2. The apparatus as set forth in claim 1 and further comprising:

amplifying means connected to the output of said multiplier, said amplifying means inverting the signal from said multiplying means.

3. The apparatus as set forth in claim 2 wherein the output of said amplifier is connected to one input of said analog multiplier means.

4. The apparatus as set forth in claim 3 and further comprising:

second analog multiplier means for producing an electrical signal proportional to the product of electrical signals;

second amplifying means;

wherein said multiplex means interconnects said plural photocell means and said second analog multiplier means in predetermined combinations; and wherein said second amplifying means is connected to the output of said second multiplying means and said amplifying means does not invert the signal from said second multiplying means.

5. The apparatus as set forth in claim 4 wherein said multiplex means selectively interconnects the output from said amplifying means and an input of said second analog multiplier means.

6. The apparatus as set forth in claim 4 and further comprising:

low pass filter means connected to the output of said second amplifying means.

7. The apparatus as set forth in claim 4 wherein said second amplifying means comprises:

an amplifier having inverting and non-inverting inputs;

a source of variable voltage connected to the inverting input;

said second multiplying means coupled to said non-inverting input; and feedback means interconnecting the output of said amplifier and said inverting input.

8. The apparatus as set forth in claim 7 wherein said source comprises a digital to analog converter.

9. The apparatus as set forth in claim 7 wherein said feedback means comprises a resistor network and second multiplex means for selectively connecting said resistor network to said amplifier.

10. Apparatus for monitoring a luminous process comprising:

photocell means for producing an electrical signal dependent upon the luminosity of said process;

analog multiplier having first and second inputs, said first input coupled to said photocell means;

amplifying means having inverting and non-inverting inputs, said inverting input being connected to an output of said analog multiplier means; and digital to analog converter means connected to the non-inverting input of said amplifying means.

11. The apparatus as set forth in claim 10 wherein the output of said amplifying means is coupled to the second input of said multiplying means.

* * * * *